United States Patent
Jacobsen et al.

[11] Patent Number: 5,807,075
[45] Date of Patent: Sep. 15, 1998

[54] DISPOSABLE AMBULATORY MICROPROCESSOR CONTROLLED VOLUMETRIC PUMP

[75] Inventors: Stephen C. Jacobsen; Clark C. Davis, both of Salt Lake City; Scott D. Miles, Sandy, all of Utah

[73] Assignee: Sarcos, Inc., Salt Lake City, Utah

[21] Appl. No.: 643,472

[22] Filed: May 6, 1996

Related U.S. Application Data

[63] Continuation-in-part of Ser. No. 157,693, Nov. 23, 1993, Pat. No. 5,632,606.

[51] Int. Cl.⁶ ............................................... F04B 49/00
[52] U.S. Cl. ..................... 417/44.2; 417/313; 417/415; 417/360; 417/63; 604/152
[58] Field of Search ...................... 417/326, 313, 417/415, 360, 44.1, 44.2, 44.4, 63; 604/151, 152

[56] References Cited

U.S. PATENT DOCUMENTS

| | | |
|---|---|---|
| 1,032,187 | 7/1912 | Clifford . |
| 2,709,118 | 5/1955 | Martin . |
| 2,766,701 | 10/1956 | Giraudeau . |
| 3,300,703 | 1/1967 | Gold et al. . |
| 3,509,890 | 5/1970 | Phillips . |
| 3,515,169 | 6/1970 | Berg et al. . |
| 3,742,822 | 7/1973 | Talbert . |
| 4,085,941 | 4/1978 | Wilkinson et al. . |
| 4,089,349 | 5/1978 | Schenk . |
| 4,095,566 | 6/1978 | Fox . |
| 4,128,227 | 12/1978 | Blomqvist . |
| 4,159,024 | 6/1979 | Getman . |
| 4,433,795 | 2/1984 | Maiefski et al. . |
| 4,549,718 | 10/1985 | Seger . |
| 4,637,295 | 1/1987 | Powers et al. . |
| 4,721,133 | 1/1988 | Sunblom . |
| 5,104,374 | 4/1992 | Bishko et al. . |
| 5,144,882 | 9/1992 | Weissgerber . |
| 5,165,874 | 11/1992 | Sancoff et al. ............................ 417/360 |
| 5,236,004 | 8/1993 | Sunderland et al. ..................... 417/360 |
| 5,266,013 | 11/1993 | Aubert et al. ............................ 417/360 |
| 5,344,292 | 9/1994 | Rabenau et al. ......................... 417/360 |
| 5,429,602 | 7/1995 | Hauser . |
| 5,464,391 | 11/1995 | DeVale ..................................... 604/151 |
| 5,558,639 | 9/1996 | Gangemi et al. ........................ 417/360 |
| 5,647,852 | 7/1997 | Atkinson .................................. 417/360 |

FOREIGN PATENT DOCUMENTS 855649  11/1952  Germany .

*Primary Examiner*—Timothy Thorpe
*Assistant Examiner*—Peter G. Korytnyk
*Attorney, Agent, or Firm*—Thorpe, North & Western, LLP

[57] ABSTRACT

An ambulatory volumetric pump apparatus includes a housing defining a channel therethrough having an inlet for receiving a fluid and an outlet for discharging a fluid, a pump operable to pump fluid through the channel, a motor for operating the pump in response to control signals, and a programmable microprocessor for selectively supplying control signals to the motor to cause the motor to operate. The programmable microprocessor is "programmed" by manually setting rotatable knobs having faces which extend through but are generally flush with the housing exterior surface. The knobs include indicia to provide a visual display of the setting of the knobs and thus of the parameters of operation of the pump. An under-pressure sensor is disposed after the inlet of the channel to detect a suction or vacuum in the channel and to signal the microprocessor if such condition is detected. An over-pressure sensor is disposed before the outlet of the channel to signal the microprocessor if greater than expected pressure is detected in the channel. The microprocessor then sounds an alarm, shuts off the motor, or both.

32 Claims, 12 Drawing Sheets

DISPOSABLE AMBULATORY MICROPROCESSOR CONTROLLED VOLUMETRIC PUMP

This is a continuation-in-part of application Ser. No. 08/157,693, filed Nov. 23, 1993, entitled VOLUMETRIC PUMP/VALVE, now U.S. Pat. No. 5,632,606.

BACKGROUND OF THE INVENTION

This invention relates to a lightweight, inexpensive ambulatory volumetric pump, suitable for a variety of uses including medical systems such as intravenous (IV) therapy systems and the like.

The intravenous administration of fluids to patients is a well-known medical procedure for, among other things, administering life sustaining nutrients to patients whose digestive tracts are unable to function normally due to illness or injury, administering antibiotics to treat a variety of serious infections, administering analgesic drugs to patients suffering from acute or chronic pain, administering chemotherapy drugs to treat patients suffering from cancer, etc.

The intravenous administration of drugs frequently requires the use of an IV pump connected or built into a so-called IV administration set including, for example, a bottle of fluid to be administered and typically positioned upside down, a sterile plastic tubing set, and a pump for pumping fluid from the bottle through the IV set to the patient. Other mechanisms may be included to manually stop the flow of fluid to the IV feeding tube and possibly some monitoring devices.

Current IV pumps generally are of two basic types: electronic pumps and disposable non-electronic pumps. Although the electronic pumps have been significantly miniaturized and do include some disposable components, they are nevertheless generally high in cost, require frequent maintenance with continued use, and may be difficult for a layman to operate if, for example, self treatment is desired.

The disposable non-electric pumps generally consist of small elastomeric bags within a hard shell container, in which the bags are filled with IV solution under pressure. The pressure generated by the contraction of the elastomeric bag forces the IV solution through a fixed orifice at a constant flow rate into the patient's vein. Although these pumps are much less expensive than the electronic pumps and eliminate the need for maintenance (since they are discarded after every use), their drawbacks include the lack of monitoring capability, the lack of the ability to select different flow rates, limited fluid capacity, and still relatively high cost for a disposable product.

SUMMARY OF THE INVENTION

It is an object of the invention to provide a new and improved volumetric pump which is especially suitable for use in IV administration sets, other medical and non-medical systems, and the like.

It is a further object of the invention to provide such a pump which is easy to manufacture and utilizes low cost parts.

It is also an object of the invention to provide such a pump which is efficient and reliable.

It is an additional object of the invention to provide such a pump which may be readily miniaturized.

It is another object of the invention to provide an ambulatory, low cost and therefore disposable pump.

It is still a further object of the invention to provide such a pump with low friction components such that it may be operated with low energy consumption.

It is still another object of the invention, in accordance with one aspect thereof, to provide such a pump whose flow or pumping rate, total time of operation, time interval between doses, etc. may be readily changed.

It is also an object of the invention, in accordance with another aspect thereof, to provide such a pump with microprocessor control of the operating parameters.

The above and other objects of the invention are realized in a specific illustrative embodiment of an ambulatory volumetric pump which includes a housing in which is defined a channel having an inlet for receiving a fluid and an outlet for discharging the fluid. Also disposed in the housing is a pump operable to pump fluid through the channel, a motor for operating the pump in response to control signals, and a programmable controller for selectively supplying control signals to the motor to cause the motor to operate and pump fluid, either intermittently or continuously.

In accordance with one aspect of the invention, the programmable controller is provided with rotatable knobs which are exposed and accessible through the housing and which, when rotated to selected positions, both establish the operating parameters for the pump and display for viewing what the selected parameters are.

In another aspect of the invention, the housing includes a base housing in which are disposed the motor and programmable controller, a casing in which is defined and disposed respectively the channel and the pump, and a clip mechanism to enable clipping the casing onto the base housing. The motor includes the drive gear exposed through a wall of the base housing and the pump includes a drive hub engageable with the drive gear, to be driven thereby, when the casing is clipped onto the base housing.

In accordance with still another aspect of the invention, the pump utilizes a simple circumferential polymeric seal, or sphincter seal, to retain and prevent loss or leaking of fluid being pumped.

BRIEF DESCRIPTION OF THE DRAWINGS

The above and other objects, features and advantages of the invention will become apparent from a consideration of the following detailed description presented in connection with the accompanying drawings in which.

DETAILED DESCRIPTION OF THE DRAWINGS

Figure 1:
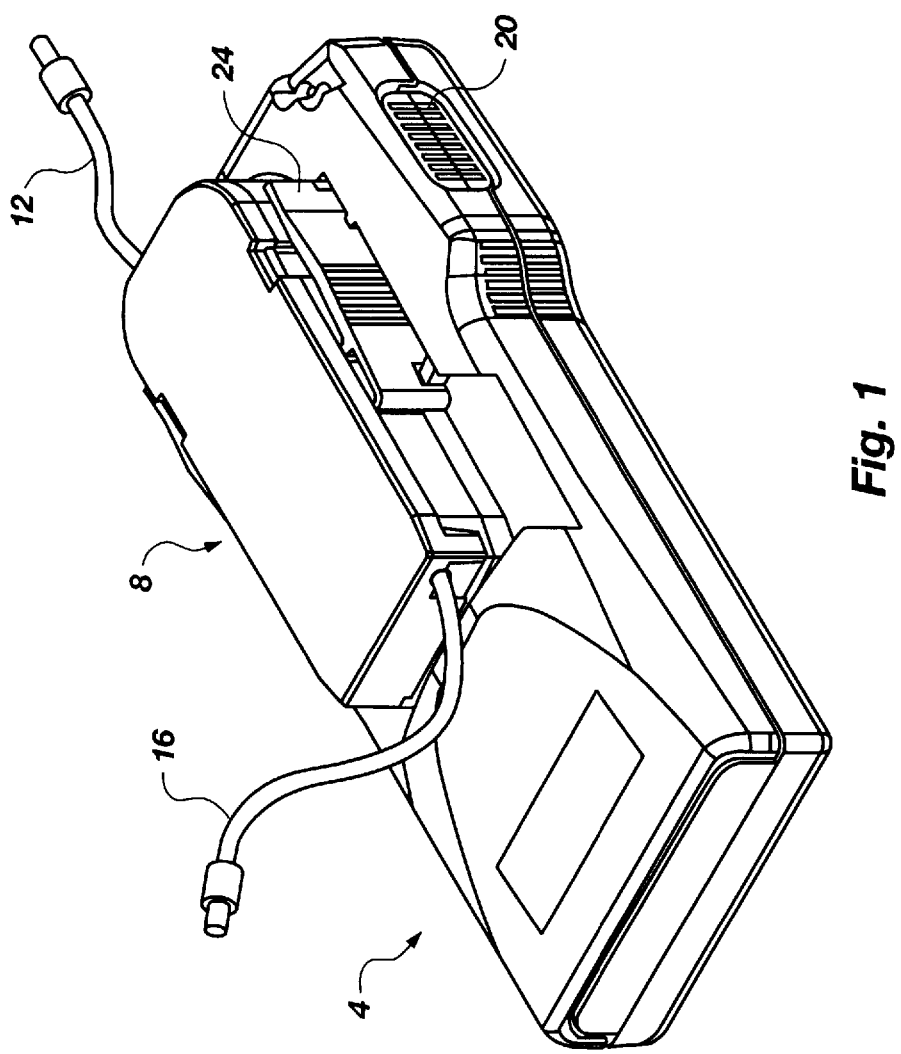
FIG. 1 is a top perspective view of an ambulatory, volumetric pump made in accordance with the principles of the present invention.

In the drawings, like parts or components will be identified by like numerals from one drawing to the next, for ease of understanding the description of the invention.

FIG. 1 is a top, perspective view of one illustrative embodiment of an ambulatory microprocessor-controlled volumetric pump having a base housing 4 in which are disposed pump driver components of the invention, including an electric motor, battery power source, and programmable microprocessor for controlling the pumping operation. Detachably mounted on the base housing 4 is a cassette (or casing) 8 in which are contained the pump mechanism, a channel through which a fluid to be delivered to a patient is pumped, and valves for controlling the flow of fluid. An inlet tube 12 is coupled to the cassette 8 to carry fluid from a source to the channel in the cassette, and an outlet tube 16 is also coupled to the cassette to carry fluid from the channel to a destination as a result of the operation of the pumping mechanism. Mounted in the side of the base housing 4 is a run/stop switch 20 by which a patient may activate the programmable microprocessor.

The cassette 8 is held in place on the base housing 4 by a pair of mounting clips 24 (see also FIG. 5) which deflect outwardly after the cassette 8 is pressed into position on the base housing 4. In particular, when the mounting clips 24 deflect outwardly, tabs 24a (FIG. 5) on the ends of the clips extend into side slots 6 formed in the sides of recess 28 on top wall 4a of the base housing 4. To release the cassette 8, the mounting clips 24 are pressed inwardly to deflect the tabs 24a inwardly, thus pulling them from the slots 6. The cassette 8 can then be removed.

Figure 2:
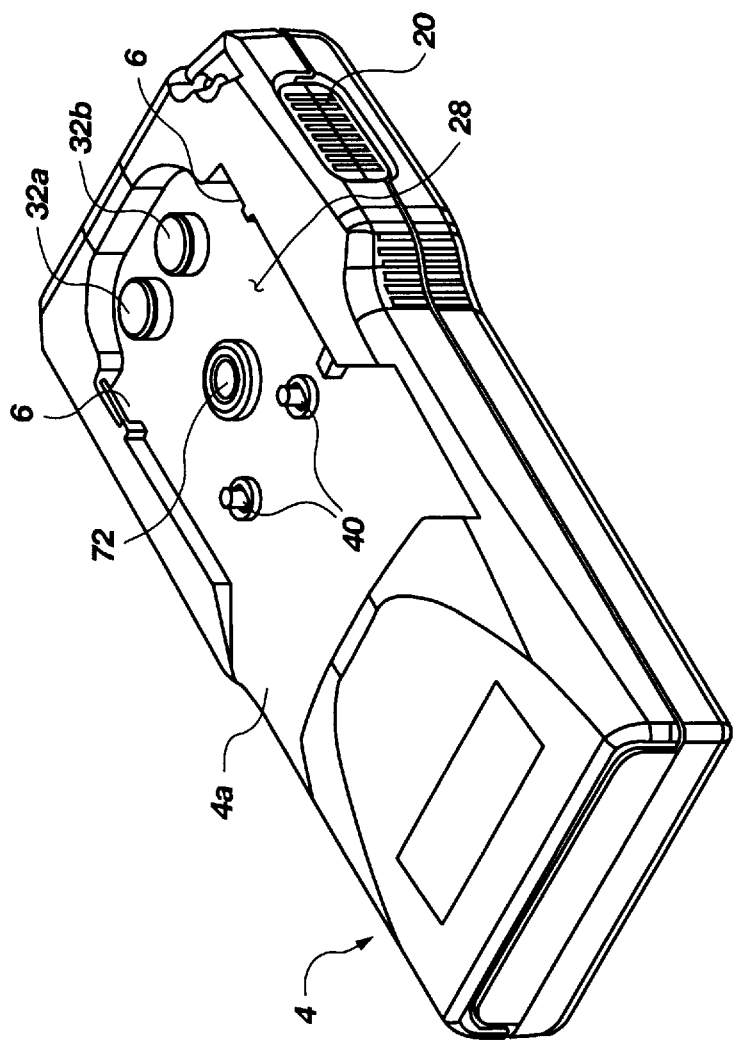
FIG. 2 is a top, perspective view of the base housing of the pump of the present invention.

FIG. 2 shows a top perspective view of the base housing 4, with the cassette removed to expose the recess 28 formed in the upper wall 4a of the base housing for receiving the cassette. Protruding through openings in the upper wall 4a of the base housing 4 are pressure sensor buttons 32a and 32b (to be discussed later), a face drive gear 72 (also to be discussed later), and valve actuator lever pins 40 which, as will be explained later, cause the selective opening and closing of valves located in the channel formed in the cassette to either allow or prevent the flow of fluid therethrough.

Figure 3:
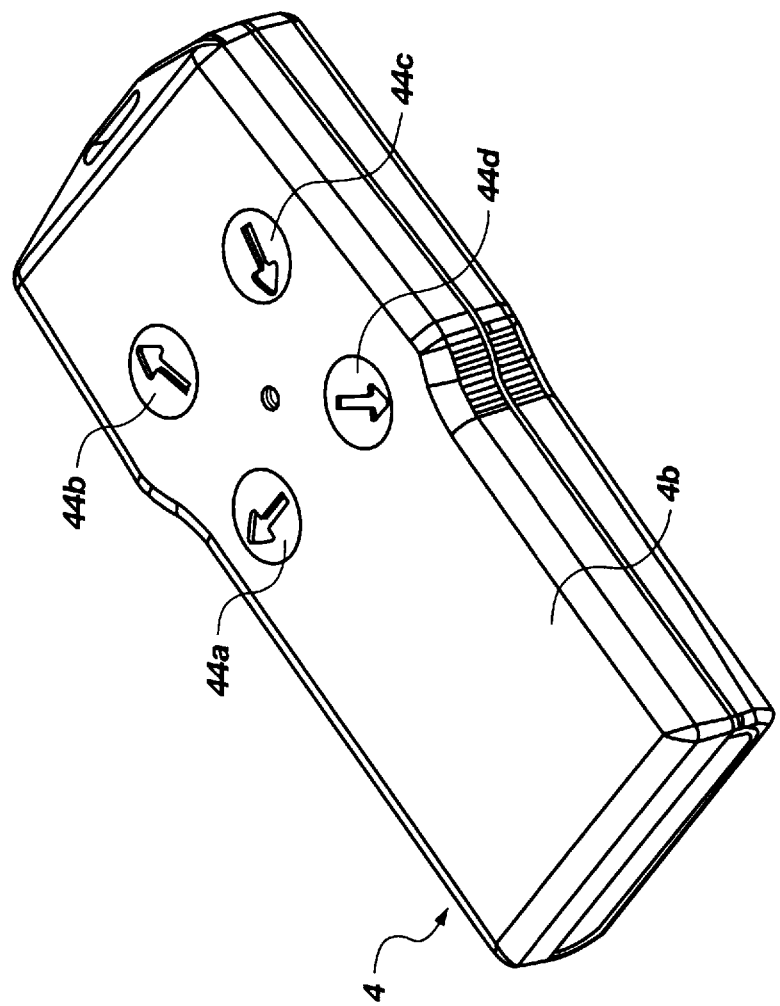
FIG. 3 is a bottom perspective view of the base housing.

FIG. 3 is a perspective view of the bottom of the base housing 4 showing four rotatable knobs 44a, 44b, 44c and 44d which are exposed through a bottom wall 4b of the housing.

The tops of the knobs 44a through 44d are substantially flush with the bottom wall 4b so that clothing or other items will not snag on the knobs and so that the knobs won't be inadvertently moved by bumping, etc. Formed in the top surfaces of the knobs 44a through 44d are recesses in the shape of arrows and into which a coin, fingernail, screw driver or other tool may be inserted to rotate the knobs to a desired position. The knobs are used to "program" a programmable microprocessor contained in the base housing 4, to operate the pump according to the parameter settings of the knobs. In other words, the rotary or angular position of each knob establishes a particular parameter of operation of the pump such as flow rate, number of doses or pump cycles over some period of time, the total dosage time, total volume of fluid to be pumped, etc.

Communication of the knob settings to the programmable microprocessor could be carried out in a variety of ways including provision of metal, conductive wipers on the underside of the knobs to press against copper patterns on a printed circuit board 94 (FIG. 4) contained in the base housing 4 in such a way that binary coded signals or bits can be read from the position of the wipers on the copper patterns by the programmable microprocessor.

It will be noted that setting the knobs 44a, 44b, 44c and 44d also provides a visual display of the parameters chosen by reason of the direction in which the recessed arrows are pointing. Labels disposed around the knobs could identify the parametric values for the various rotary positions of the knobs.

Figure 4:
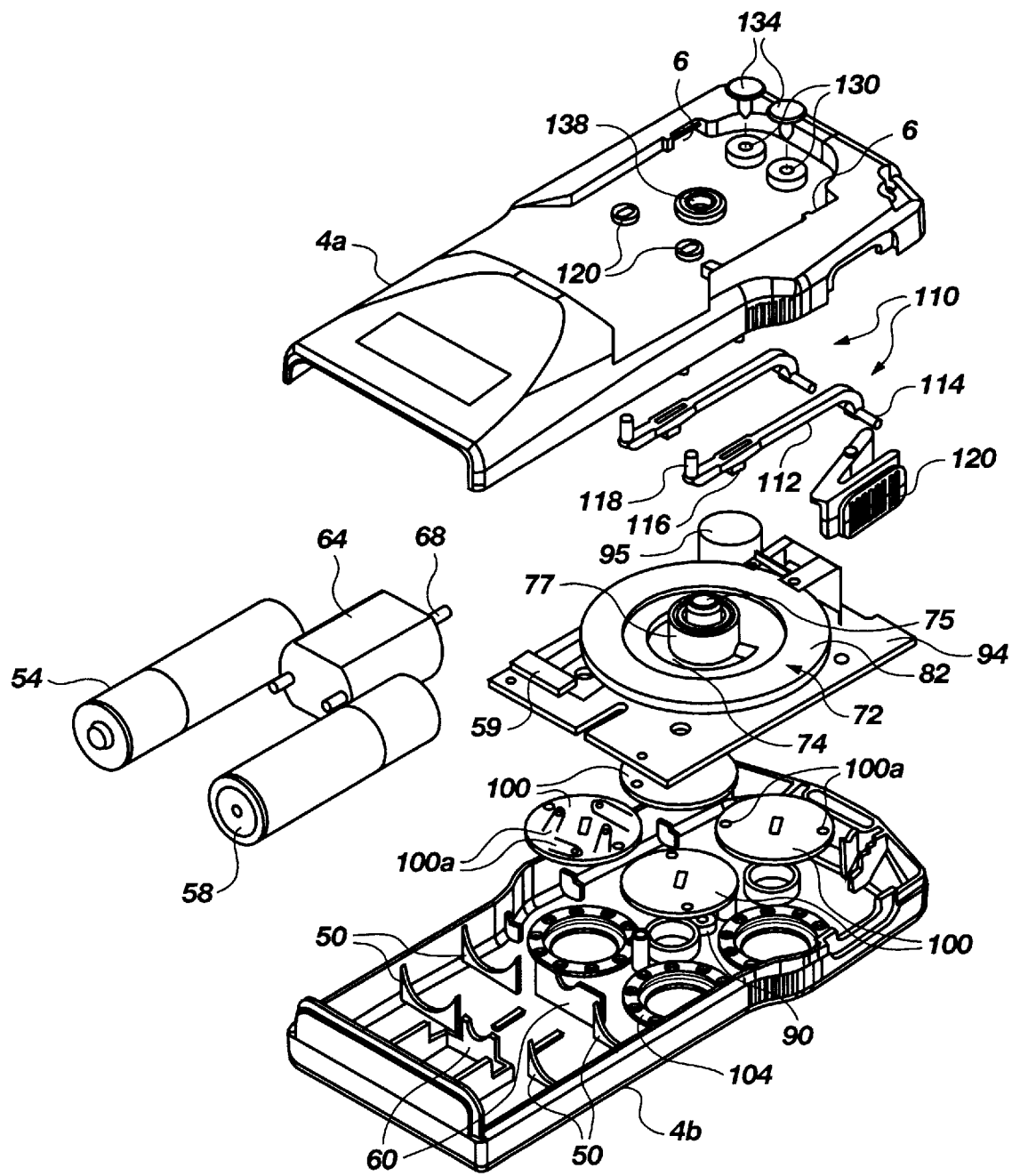
FIG. 4 is an exploded view of the base housing and components contained therein.

Referring now to FIG. 4, there is shown a top, exploded view of the base housing 4 to include the top wall 4a and bottom wall 4b. Brackets 50 are formed in the bottom wall 4b for receiving and holding batteries 54 and 58 which are the power source for operating the programmable microprocessor 59 and motor which causes operation of the pump. Brackets 60 are also formed in the bottom wall 4b for receiving and holding a miniature electric motor 64. A motor drive shaft 68 (and pinion gear) extends forwardly of the motor 64 to engage and cause a face drive gear 72 to rotate when the motor 64 is operated.

Figure 12:
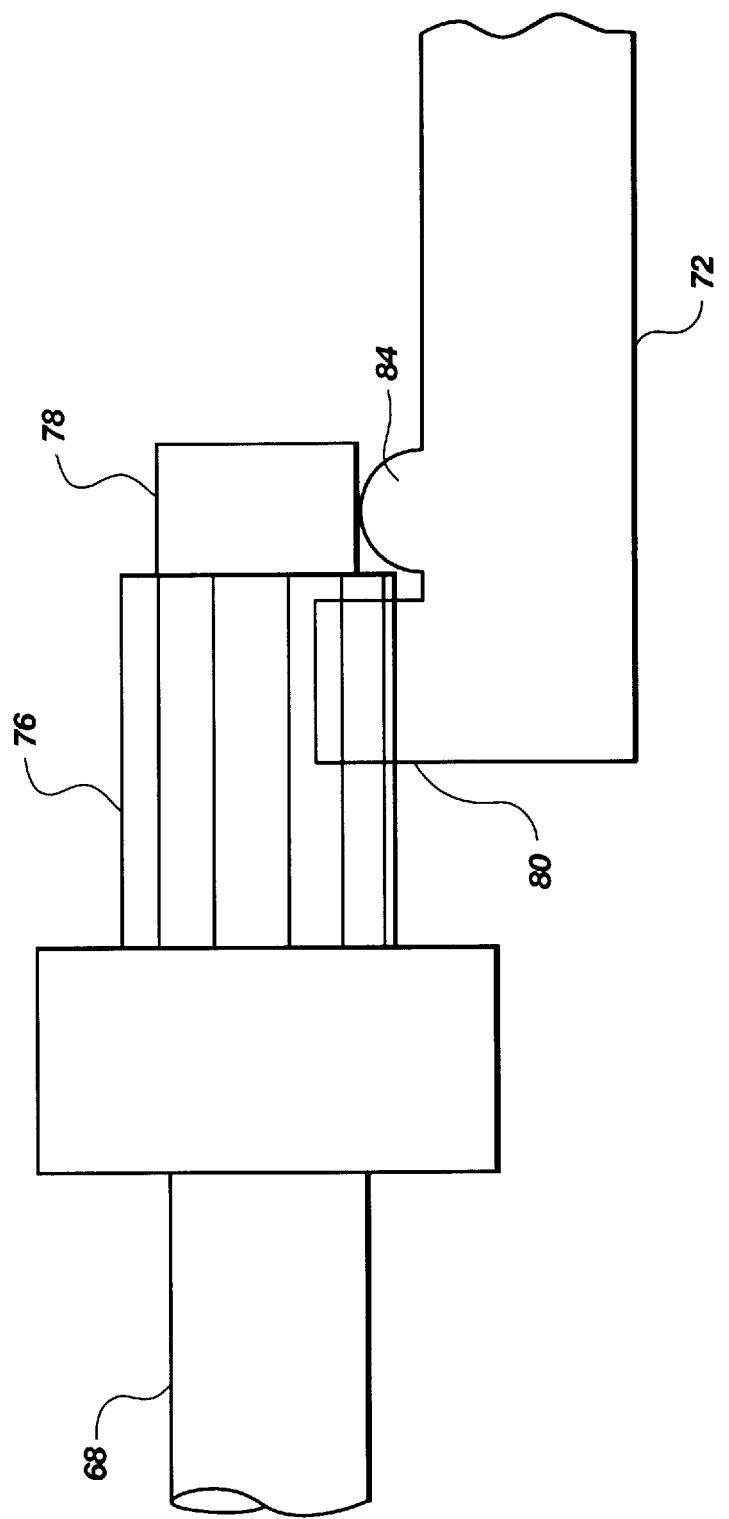
FIG. 12 is a fragmented, side graphic representation of the motor drive shaft and pinion gear, and face drive gear of the present invention.

FIG. 12 shows a fragmented, cross-sectional view of a portion of the motor drive shaft 68 on the end of which is mounted a pinion gear 76 with a roller extension 78. The pinion gear teeth mesh with gear teeth 80 formed at the edge of the face drive gear 72 to extend axially thereof, as seen in FIG. 12. Formed inside the face gear teeth 80 to extend circumferentially on the face drive gear 72 is an annular bead 84 over which the roller 78 rolls, as the motor drive shaft 68 rotates to thus rotate the pinion gear and cause the face drive gear to rotate. The contact of the roller 78 and the annular bead 84 maintains the pinion gear teeth 76 a certain distance apart from the face gear teeth 80 and this, in turn, reduces friction between the two gears and reduces noise. With reduced friction, energy consumption is also reduced. (Note that in the FIGS. showing the entire base housing, the face drive gear 72 is shown on top of the pinion gear 76.)

Figure 10A:
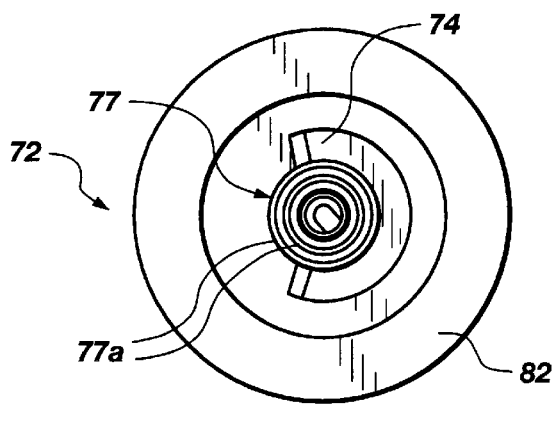
FIGS. 10A–10E show different views of an illustrative embodiment of a face drive gear suitable for use in the present invention.
Figure 10B:
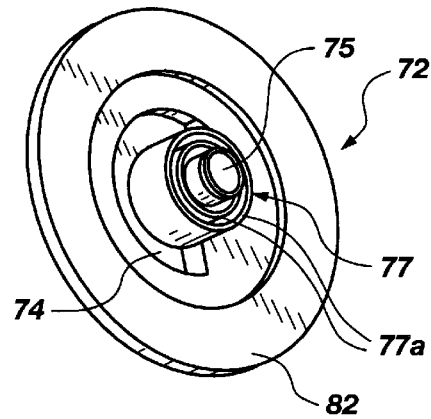
Figure 10C:
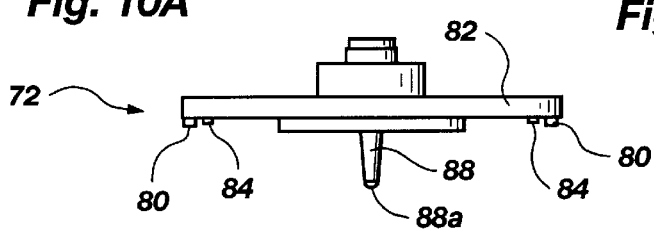
Figure 10D:
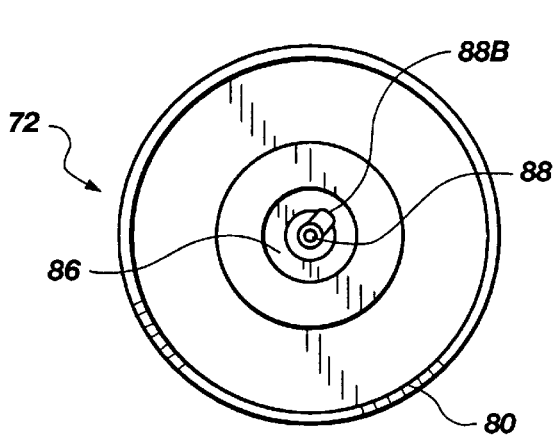
Figure 10E:
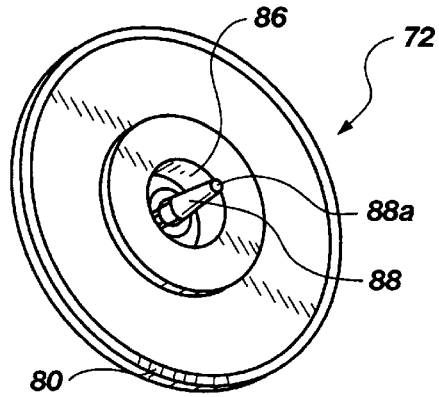

The face drive gear 72 is shown in greater detail in FIGS. 10A–10E. The gear 72 includes a disk 82 on the outer edge of which are formed the gear teeth 80 on the underside thereof, as best seen in FIGS. 10D and 10E. As previously described, the annular bead 84 is located just inside (but could be outside) the gear teeth 80. A central recess 86 is formed on the underside of the disk 82 and a spindle 88 extends downwardly from the recess 86 (FIG. 10C) to terminate generally in a spherical tip 88a. The spindle 88 rotatably supports the face drive gear 72 in a bearing cup 90 which is disposed on the bottom wall 4b of the base housing 4 (FIG. 4). In particular, the spindle 88 of the face drive gear 72 extends through an opening in a circuit board 94 to the bearing cup 90 to enable rotation of the face drive gear.

Figure 13:
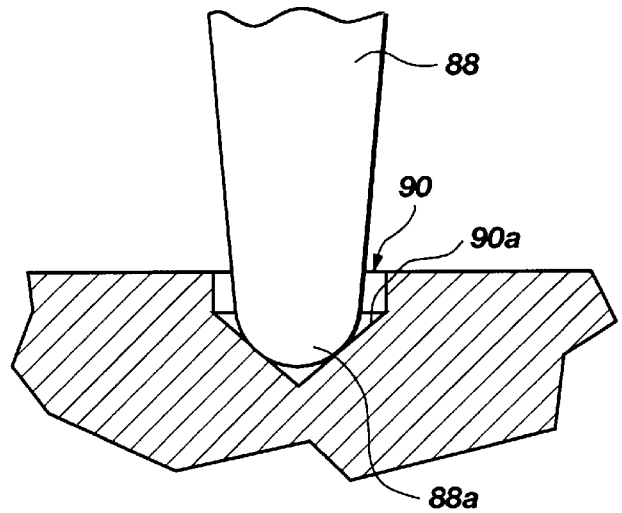
FIG. 13 is a fragmented, side cross-sectional view of the face gear spindle and support gear cup used in the present invention.

FIG. 13 shows a side, cross-sectional view of the lower end of the spindle 88 and tip 88a disposed in the bearing cup

90. Side walls 90a of the bearing cup 90 are in the shape of an inverted cone so that the contact surface between the spherical tip 88a and the side walls 90a is small, and this reduces friction in the rotation of the face drive gear 72 and thus reduces power consumption in the operation of the pump. Other features of the face drive gear 72 will be discussed later.

Returning now to FIG. 4, there are shown four programming disks 100, each of which is coupled to a respective programming knob so as to be rotated when the knob is rotated and thus allow for developing different electrical contact patterns with electrical contacts on the underside of the circuit board 94. These electrical contact points are disposed so that when electrical contacts 100a on the disks 100 contact different ones of the contact points, different settings for the programming knobs can be detected by the microprocessor 59.

The circuit board 94 is mounted on the bottom wall 4b of the base housing 4 and, as earlier indicated, the programmable microprocessor 59 for controlling operation of the pump is mounted on the circuit board as is other circuitry for carrying signals to and from the microprocessor.

Formed in the top surface of the face drive gear 72 is a cam track 74 (see FIGS. 4, 10A and 10B) on which rides and follows a pair of valve actuator levers 110. Each lever 110 includes an elongate beam 112, a pivot axle 114 disposed at generally a right angle at one end of the beam, a cam follower roller 116 rotatably mounted to project below the lower surface of the beam 112 to ride on and follow the cam track 74, and a lever pin 118 projecting upwardly from the end of the beam 112 opposite the location of the axle 114 to extend through openings 120 formed in the top wall 4a of the base housing. The construction and mounting of the valve actuation levers 110 can also be seen in side view in FIGS. 9A and 9B. As the face drive gear 72 is rotated, the levers 110 are caused to alternately pivot upwardly once for each revolution of the face gear, to cause the opening of inlet and outlet valves to be described later.

Figure 11A:
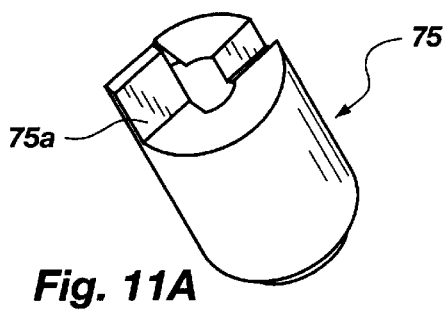
FIGS. 11A and 11B are perspective views of drive and driven hubs by which the motor operates the pump in the present invention.
Figure 11B:
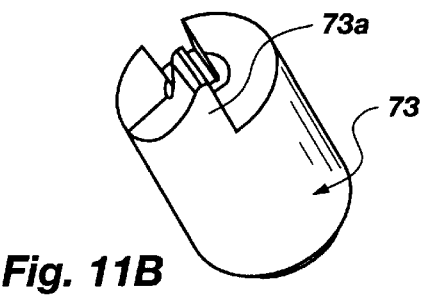

Also disposed on the upper side of the face drive gear 72 is a drive hub 75, surrounded by a capillary labyrinth seal 77. The drive hub 75 is designed to mate with a corresponding driven hub coupled to a crank shaft used to drive the pump. The detailed construction of the drive hub 75 is shown in FIG. 11A, with the driven hub 73 shown in FIG. 11B. Both hubs include a drive tang 75a and 73a for engaging and rotationally driving the drive tang on the mating hub. The hub 73 of FIG. 11B can be viewed as being inverted and placed on top of the hub 75 of FIG. 11A. In this configuration, when the hub 75 is rotated counter clockwise looking down, it is apparent that the hub 73 would likewise be rotated in that direction. Note that the hub 75 of FIG. 11A engages the hub 73 of FIG. 11B at only one angular position, i.e., when the drive tang 75a of the hub 75 engages the drive tang 73a of the hub 73 so that the two drive hubs, when in the operating position, are always at the same relative angular position with respect to one another.

Figure 8:
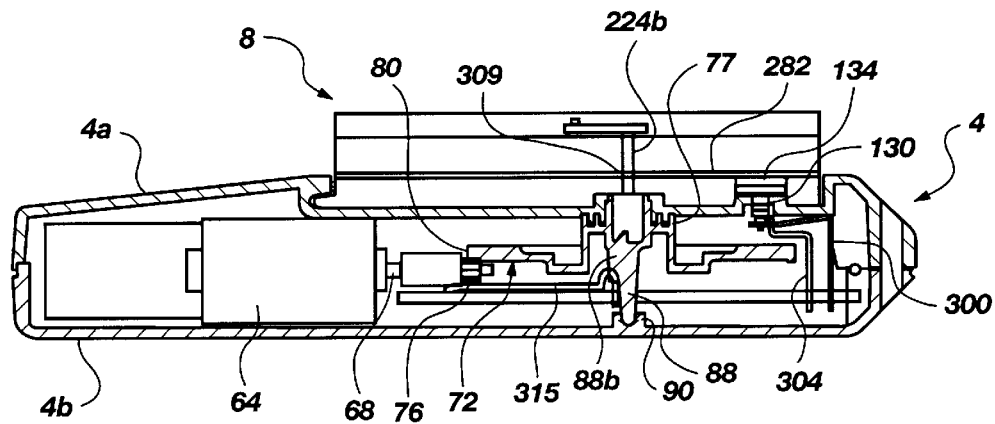
FIG. 8 is a side, cross-sectional view of the cassette mounted on the base housing, showing various components.
Figure 14:
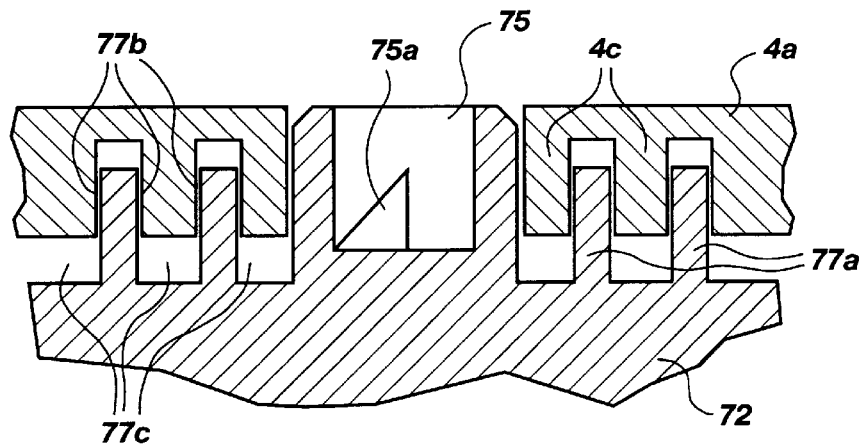
FIG. 14 is a fragmented, side cross-sectional view of an illustrative capillary labyrinth seal used in the present invention.

The capillary labyrinth seal 77 is also shown in greater detail in FIGS. 10A, 10B and 14 to include a plurality of concentric annular walls 77a which, when the face drive gear 72 is installed in the base housing 4, are annularly interleaved with complimentary annular walls 4c (FIG. 14) formed on the underside of the upper wall 4a of the base housing 4. This interleaving or meshing of the capillary labyrinth seal 77 with complimentary annular walls 4c in the bottom surface of the upper wall 4a of the base housing 4 is also shown in FIG. 8. The purpose of the capillary labyrinth seal 77 is to prevent water or other fluids from entering the interior of the base housing 4 at locations where access to the base housing from the cassette 8 is required. With the capillary labyrinth seal 77 of the present design, liquid is drawn into narrow "capillary traps" 77b (FIG. 14) and then is prevented from exiting these traps by the larger "capillary breaks" or reservoirs 77c formed by gaps between the capillary labyrinth walls 77a and the base housing annular walls 4c. Thus, any liquid in the capillary traps 77b tends to stay in those traps since the capillary action there relative to the capillary attraction in the capillary breaks or reservoirs 77c is much greater. If any liquid manages to get through the capillary traps 77b, then it would fill the capillary break or reservoir area 77c before it would proceed any further.

Referring once again to FIG. 4, two openings 130 are shown formed in the upper wall 4a of the base housing 4 for receiving what will be referred to as over/under-pressure sensor buttons 134 (to be described later). Finally, an opening 138 is formed in the upper wall 4a for receiving and providing access to the hub 75 of the face drive gear 72, to engage a driven hub and crank shaft located in the cassette 8.

Figure 5:
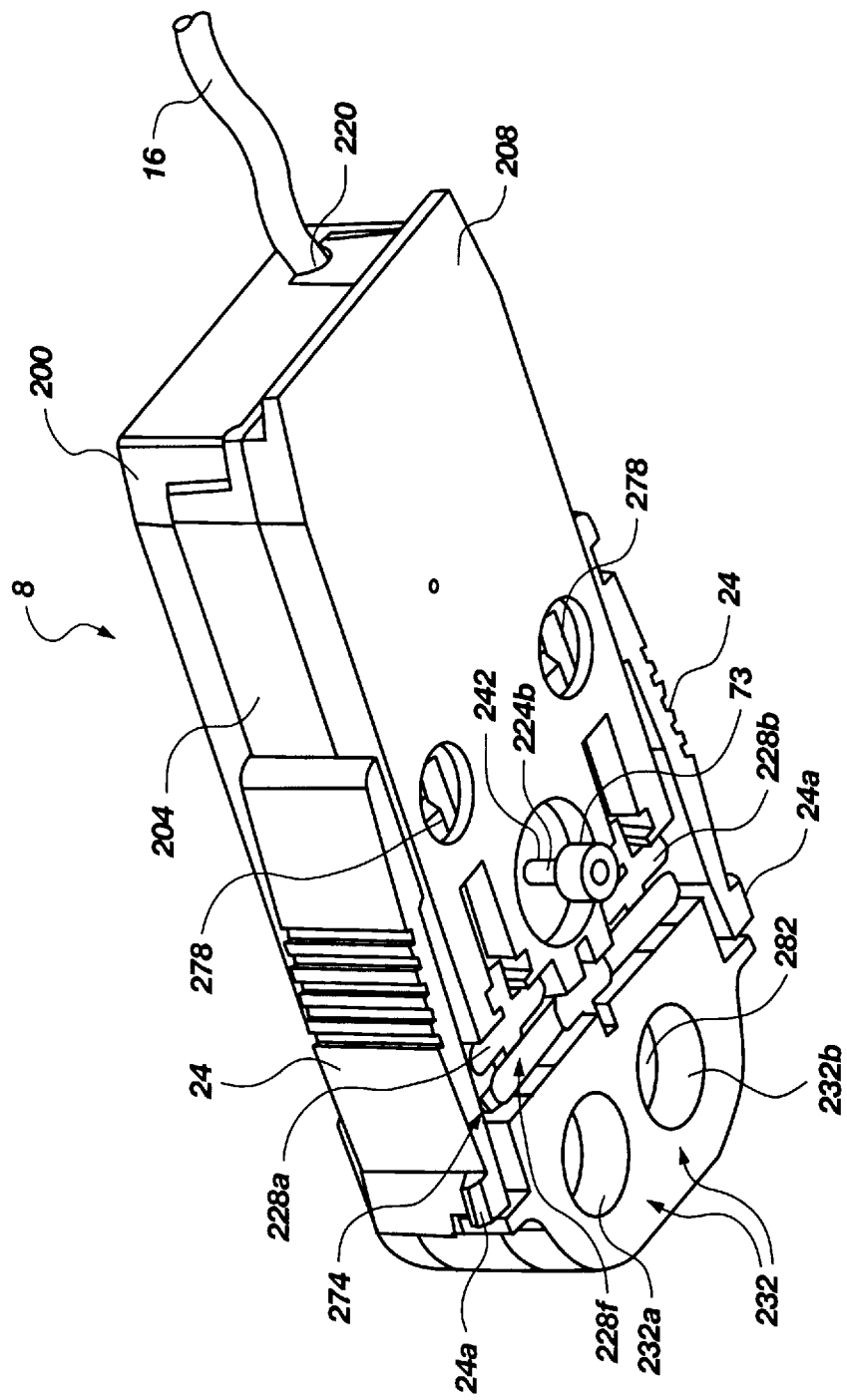
FIG. 5 is a bottom perspective view of the cassette of the pump of the present invention.
Figure 6:
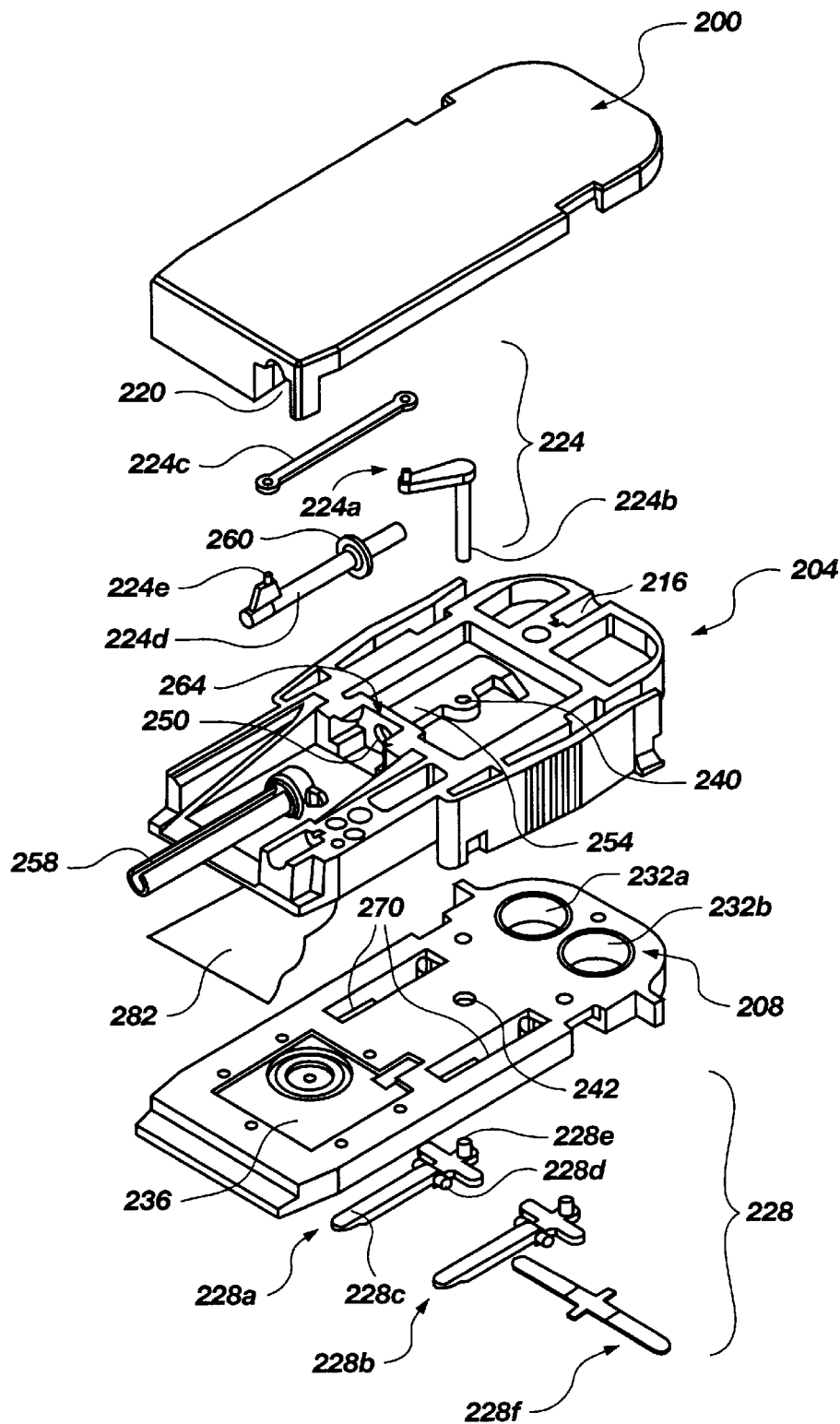
FIG. 6 is a top exploded view of the cassette.
Figure 7:
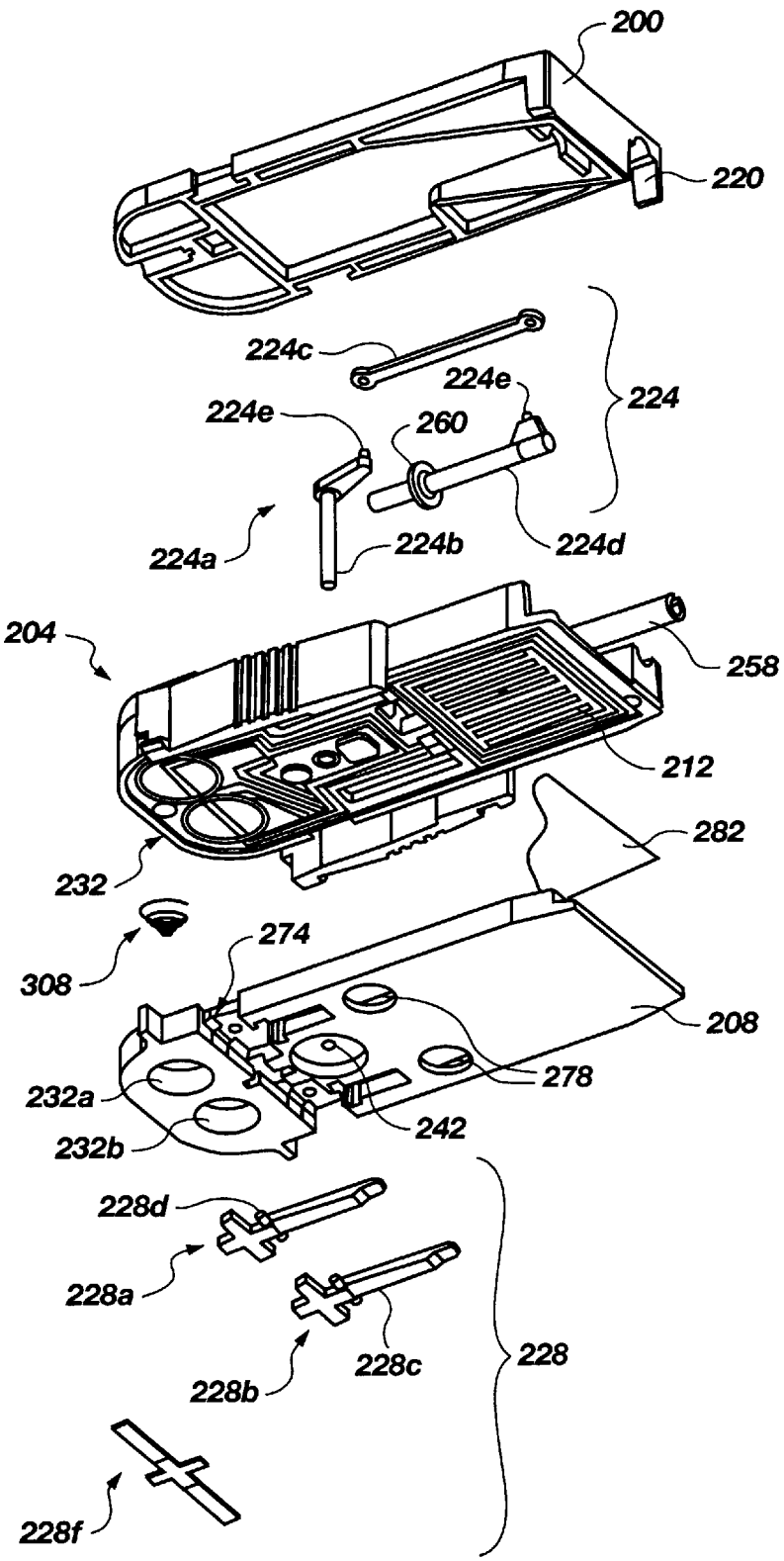
FIG. 7 is a bottom exploded view of the cassette.

FIGS. 5, 6 and 7 show the cassette 8 from a bottom perspective view, a top perspective exploded view, and a bottom perspective exploded view, respectively. The cassette 8 is composed of a top cover 200, a main body 204 and a bottom cover 208. A channel system 212 (FIG. 7) is formed on the underside of the body 204 and partially on the top of bottom cover 208 for receiving fluid through an inlet 216 (FIG. 6), for pumping to an outlet 220 (FIGS. 5 and 7).

The cassette 8 also contains a pump mechanism 224 mounted in and on the upper side of the body 204 (FIGS. 6 and 7), a valve system 228 for controlling the flow of fluid through the channel system 212, over- and under-pressure sensors 232 (FIGS. 5 and 7) and an air elimination and fluid filter chamber 236 (FIG. 6). The pump mechanism 224 includes a crank 224a whose crank shaft 224b extends through an opening 240 in the body 204 and an opening 242 in the bottom cover 208 to protrude some distance below the bottom cover as best seen in FIG. 5. A driven hub 73, previously discussed, is disposed on the end of the crank shaft 224b (FIG. 5). As previously discussed, the driven hub 73 is engaged by a drive hub 75 (FIG. 4) contained on the face drive gear 72 which, in turn, is driven to rotate by a pinion gear 76 (FIG. 12) and motor 64 (FIG. 4). The crank 224a is thus caused to rotate whenever the motor is operated.

The pump mechanism 224 also includes a connecting rod 224c and a piston 224d. The crank 224a is pivotally coupled to one end of the connecting rod 224c, and the other end of the connecting rod is pivotally coupled to a connecting nipple 224e on the piston 224d (FIGS. 6 and 7). The piston 224d is slidably disposed through an aperture 250 into a pumping chamber 254, and is slidably held in a piston guide 258 (FIG. 6). A piston sphincter seal 260 is shown disposed about the piston 224d in FIGS. 6 and 7, but this seal would be positioned in front of the aperture 250 in a holding cavity 264. The seal 260 prevents the leaking of fluid from the chamber 254 during the pumping action and yet is very low drag so that energy consumption during pumping is minimized.

Figure 15:
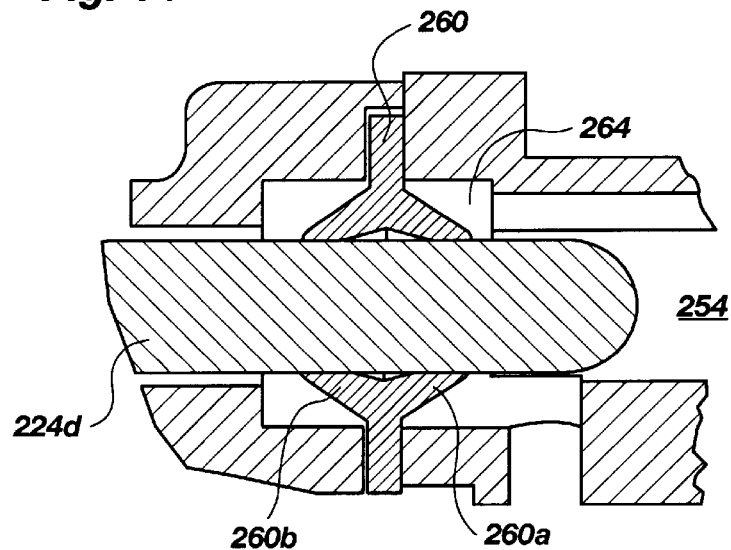
FIG. 15 is a fragmented, side cross-sectional view of the piston sphincter seal of the present invention.

FIG. 15 shows a side, cross-sectional view of the piston sphincter seal 260 disposed in the holding cavity 264, the seal including a forwardly extending branch 260a and a rearwardly extending branch 260b, both surrounding and in contact with the piston 224d. When the crank 224a is rotated to cause the connecting rod 224c to move the piston 224d, the piston reciprocates in and out of the pumping chamber 254 to pump fluid through the cassette 8.

The valve system 228 is shown in FIGS. 6 and 7 to include a pair of valve levers 228a and 228b, each having a beam 228c, a pivot axis 228d and a valve closure nipple 228e (FIG. 6). The valve levers 228a and 228b are pivotally mounted in the bottom cover 208 to fit in slots 270 (FIG. 6) a leaf spring 228f is press fitted into a slot 274 formed on the bottom side of the bottom cover 208 (FIGS. 5 and 7). The spring 228f presses against the underside of the beams 228, just under the location of the valve closure nipples 228e to force the nipples upwardly to normally close respective valves (to be described later). In order to open the valves, the end of the beams 228c opposite the location of the nipples 228e are moved upwardly (to pivot the nipples downwardly) by corresponding lever pins 118 of valve actuation levers 110 (FIG. 4). The lever pins 118 extend through corresponding openings 278 of the bottom cover 208, to contact the levers 228a and 228b to effect the opening of the valves.

The over- and under-pressure sensors 232 include openings 232a and 232b through which pressure sensor buttons 134 (FIGS. 4 and 8) extend to contact a gasket or membrane 282 over which fluid flows into the cassette 8 and out of the cassette 8. When pressure downstream of the outlet 220 of the cassette 8 increases, indicating a blockage in the tubing, for example, the membrane 282 bulges toward one of the buttons 134 and that button is moved to push a moveable contact spring to make electrical contact with a stationary contact on the circuit board 94 to indicate to the programmable microprocessor 59 that an "over pressure condition" exists downstream from the outlet. The microprocessor 59 could then sound an alarm 95 (FIG. 4), stop the pumping or both. If, for example, a blockage has occurred in tubing upstream of the inlet 216 of the cassette 8, and the pump either has operated or is operating, a vacuum will occur in the channel near the inlet causing another portion of the membrane 282 to be drawn further into the channel (opposite bulging) and a corresponding button 134 moves slightly toward the channel to indicate to circuitry on the circuit board 94 and the programmable microprocessor 59 that an upstream blockage has occurred. The alarm 95 could then be sounded and/or the pumping stopped, as with the over-pressure sensing. This will all be further described when discussing the other FIGS.

The air elimination and fluid filter chamber 236 (FIG. 6) provides for elimination of air from the fluid flowing in the channel in the cassette 8 and for filtering the fluid to remove contaminants, etc. This will be discussed later.

The membrane gasket 282 is disposed to cover a substantial portion of the underside of the body 204 of the cassette 8 to define (form one side of) the channel which extends through the cassette. The gasket 282 also allows for operation of the flow control valves and the over- and under-pressure sensors, as well as providing a sterility seal 309 around the rotating crank shaft 224b.

FIG. 8 is a cross-sectional view of the base housing 4 showing the motor 64, pinion gear 76 mounted on the motor drive shaft 68, and face drive gear 72 whose gear teeth 80 are meshing with the pinion gear teeth 76, as previously described. The spindle 88 of the face drive gear 72 is rotationally supported in bearing cup 90. Pressure sensor button 134 is shown disposed in opening 130, with the upper end of the button substantially in contact with membrane 282. When the membrane 282 is subject to an over-pressure in the fluid with which it is in contact, it deforms to press against the button 134, causing the button to push against a contact spring 300 which, itself is thus deflected to signal the programmable microprocessor 59 that an over-pressure situation has been detected downstream of the outlet. When contact spring 300 is sufficiently deflected, it makes electrical contact with a stationary contact on the circuit board 94, and this electrical contact is detected by the microprocessor 59. The under-pressure sensor operates in a similar manner except that a spring 308 (see FIG. 7) is positioned above the membrane 282 to cause the membrane to push down against a different pressure sensor button and thus apply a force to a different portion of the contact spring 300. Then, if an under-pressure condition occurs upstream of the inlet, the membrane 282 would be drawn away from the button thus compressing under-pressure spring 308 (because of the vacuum created by the pumping action), and this would cause the button to relieve force on the contact spring. This condition would be detected and the programmable microprocessor alerted that an under-pressure condition has occurred.

The under-pressure portion of the contact spring 300 normally makes contact with stationary contact 304 when no cassette 8 is clipped onto the base housing 4. When the cassette 8 is clipped onto the base housing, an under-pressure spring 308 (FIG. 7) pushes the membrane 282 outwardly against one of the buttons 134. This button thus presses down against the under-pressure portion of contact spring 300 such that it breaks its electrical connection to stationary contact 304. Then, when the cassette 8 is removed, or when an upstream under-pressure condition occurs, this under-pressure portion of the contact spring 300 is allowed to move back to its original position making contact with the stationary contact 304. When this contact closure is sensed by the microprocessor 59, it may sound an alarm 95 or take other appropriate action.

The over-pressure portion of the electrical contact spring 300 normally does not make contact with the stationary contact 304. An over-pressure condition downstream of the sensor, causes the membrane 282 to bulge outwardly, as previously explained, and push against and move button 134 which, in turn, deflects the over-pressure portion of the electrical contact spring 300. When spring 300 deflects sufficiently, it makes contact with the stationary contact 304, and this electrical contact is sensed by the microprocessor 59 which can then take appropriate action.

FIG. 8 also shows a lobe 88b formed on one side of the face drive gear spindle 88 to move a contact spring 315 away from a contact on the P.C. board 94 once upon each revolution. Deflection of the motor contact spring 315 breaks an electrical supply line to the motor 64 and microprocessor 59 that it has done so. Thus after each revolution of the face drive gear 72, the motor is automatically turned off. The programmable microprocessor 89 then starts (by bypassing the motor contact spring's open connection) the motor for the next dosing, depending upon the dosing schedule "programmed" into the microprocessor.

Figure 9A:
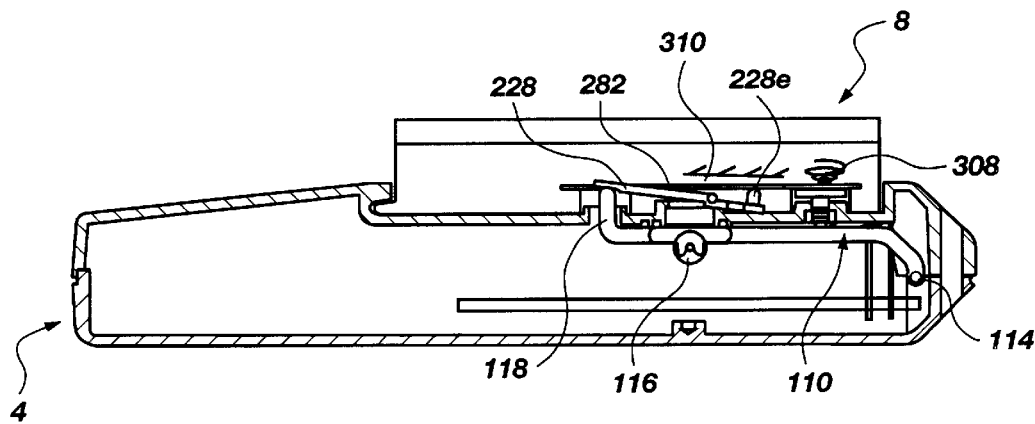
FIGS. 9A and 9B are side, cross-sectional views of the pump of the present invention, showing a flow control valve in the open position and closed position respectively.
Figure 9B:
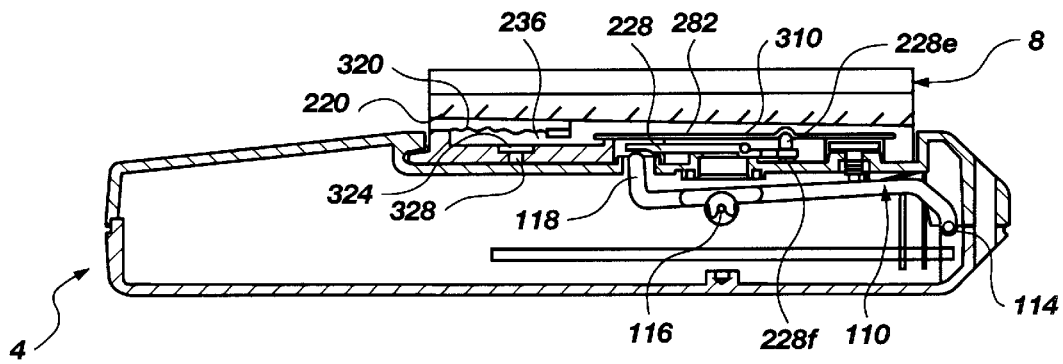

FIGS. 9A and 9B show side, cross-sectional views of the base housing 4 and cassette 8 in which a flow control valve is open and a flow control valve is closed, respectively. Referring now to FIG. 9A, one of the valve actuator levers 110 is shown pivoted upwardly (as a result of cam roller 116 riding upwardly on the cam track) to push the rear end of one of the valve levers 228 upwardly, causing valve closure nipple 228e to move downwardly to release the membrane 282 so that the channel 310 carrying fluid is opened.

As the face drive gear (not shown) continues to rotate, the cam track formed on the drive gear curves downwardly so that the cam roller 116 is allowed to move downwardly, as illustrated in FIG. 9B. The lever pin 118 of the valve actuation lever 110 is thus moved downwardly to release the valve lever 228, allowing the valve lever return spring 228f to push the valve closure nipple 228e upwardly to deform the membrane 282 and push it into the channel 310 pathway to block the flow of fluid. In the manner described, the membrane 282 is alternately deformed, to block the flow of fluid, and released, to allow the flow of fluid, with the flow being blocked in the normal position of the valve. Of course, two valves are utilized to control the flow of fluid, one near the inlet of the channel and one near the outlet.

Referring now to FIG. 9B, there is shown a cross-sectional view of the air elimination and fluid filter chamber 236 to include a hydrophilic filter membrane 320 and a hydrophobic membrane 324 covering an opening 328 to the outside. Fluid flowing in the channel 310 flows into the chamber 236 and the hydrophobic membrane 324 allows air in the fluid to diffuse through the membrane to the exterior of the housings, but does not allow fluid to pass. On the other side of the chamber 236 is the hydrophilic membrane 320 which serves two purposes—it allows fluid but not air to pass through and also filters the fluid. Illustratively, the pore size of the hydrophilic membrane is 1.2 microns and the surface area of the membrane is 4.0 square centimeters.

Figure 16:
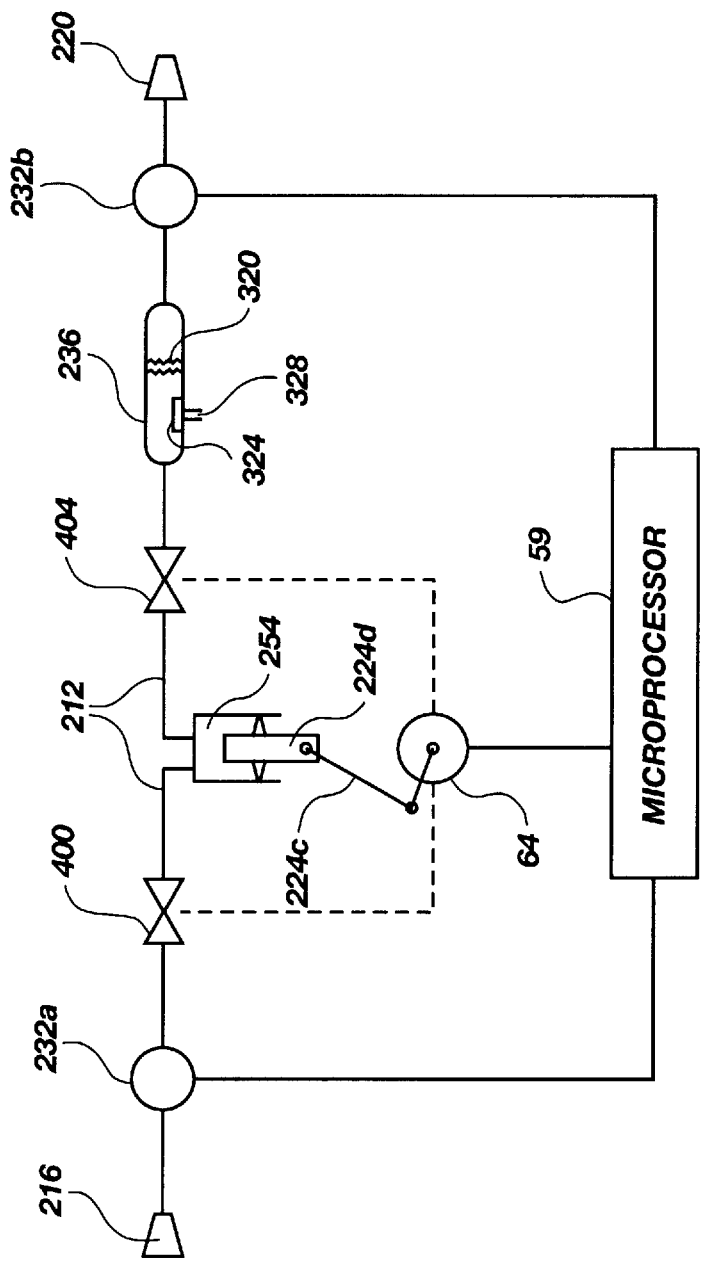
FIG. 16 is a schematic view of the flow channel, pump, valves, pressure sensors, and filters of the present invention.

FIG. 16 shows a schematic view of some of the principal components of the present invention including the channel 212 which extends through the cassette, with the channel having an inlet 216 and an outlet 220. An under-pressure sensor 232a is shown disposed in the channel to signal the microprocessor 59 if a suction occurs at that location in the channel (for example because of an occlusion upstream). The fluid flows from the under-pressure sensor 232a to an inlet valve 400 which is opened and closed mechanically, as previously described, by rotation of the face drive gear 72 (not shown in FIG. 16) under power of the motor 64. The pump mechanism 224 alternately draws fluid through the inlet valve 400 into the pump chamber 254 and then pumps the fluid out of the pump chamber and through an outlet valve 404 which will then have been opened by rotation of the face drive gear 72. From there, the fluid flows through the air elimination and fluid filter chamber 236 and then to the over-pressure sensor 232b. If an over-pressure occurs, the microprocessor 59 is signalled, as earlier described. The fluid then flows out the outlet 220. The microprocessor 59 could be any suitable type of microprocessor such as a MC 68HC05 model manufactured by Motorola.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. Ambulatory volumetric pump apparatus comprising
   channel means having an inlet for receiving a fluid, and an outlet for discharging the fluid,
   pump means operable to pump fluid through the channel,
   a pump chamber coupled into the channel means, and having a first opening for allowing fluid to flow into the chamber, a second opening for allowing fluid to flow out of the chamber, and a third opening for disposing the pump means therein,
   motor means for operating the pump means in response to control signals, and
   programmable control means for selectively supplying control signals to the motor means to cause the motor means to operate, the programmable control means providing means for varying one or more pumping parameters.

2. Apparatus as in claim 1 further including a housing in which the channel means, pump means, motor means and control means are disposed.

3. Apparatus as in claim 2 wherein said control means includes manually manipulable means for varying one or more of the pumping parameters selected from the group consisting of flow rate, total dosage time, number of doses or pump cycles over some period of time, and total volume of fluid to be pumped.

4. Apparatus as in claim 3 wherein said manually manipulable means comprise rotatable knobs having top faces which are generally flush with a housing exterior surface.

5. Apparatus as in claim 4 wherein said knobs have inscribed on the top faces indicia which provide a visual display of the setting of the knobs.

6. Apparatus as in claim 2 wherein said housing comprises
   a base housing in which are disposed the motor means and programmable control means,
   a casing in which are disposed the channel means and pump means, and
   clip means to enable clipping the casing onto the base housing,
   said motor means including a drive means exposed through an opening in a base wall of the base housing, and
   said pump means including a driven hub engageable with said drive gear, to be driven thereby, when the casing is clipped onto the base housing.

7. Apparatus as in claim 6 wherein said drive means and driven hub are rotatable generally about the same axis of rotation, wherein the drive means includes a gear drive tang means, and wherein the drive hub includes a hub drive tang means engageable for driven rotation by the gear drive tang means at the same relative angle of rotation from one engagement to another.

8. Apparatus as in claim 6 further including means disposed on the base housing for signalling the programmable control means when the casing is clipped onto the base housing.

9. Apparatus as in claim 6 further including seal means disposed about the drive means to rotate therewith, said seal means including a plurality of first concentric walls, and wherein the base housing includes a plurality of second concentric walls formed on an inside surface of said base wall about said opening, to fit and mesh between the first concentric walls to prevent entry of liquid into the base housing through said opening.

10. Apparatus as in claim 9 wherein the intermeshing walls of the seal means and the base wall are spaced so as to produce a capillary action when exposed to liquid.

11. Apparatus as in claim 6 wherein said motor means further includes a drive shaft and a pinion gear mounted on the drive shaft to rotate about a first axis when the motor is operated, and wherein said drive means comprises a disk mounted to rotate about a second axis which is generally perpendicular to the first axis, said disk including gear teeth disposed circumferentially on the disk to extend axially thereof to mesh with the pinion gear and cause rotation of the disk when the pinion gear is rotated.

12. Apparatus as in claim 11 wherein said drive means further includes an annular bead disposed concentrically with respect to the disk gear teeth, and wherein said motor means further includes roller means disposed adjacent the pinion gear to rotate therewith, and to maintain rolling contact with the annular bead to thereby establish and maintain a predetermined spatial relationship between the pinion gear and disk gear teeth.

13. Apparatus as in claim 6 wherein said casing includes a body in which at least a portion of the channel means is formed on an underside thereof, and in which the pump means is disposed on the body,
   a top cover disposed over an upper side of the body,
   a bottom cover disposed over the underside of the body, and
   a gasket membrane disposed on at least a portion of the body, and between the body and the bottom cover, to form one side of at least a portion of the channel means.

14. Apparatus as in claim 13 wherein said pump means includes a pump crank shaft which, when rotated, drives the pump means and which extends through the gasket membrane to couple to the driven hub, said gasket membrane forming a sterility seal about the pump crank shaft.

15. Apparatus as in claim 13 further including over-pressure sensing means disposed adjacent a part of the gasket membrane forming a side of the channel means, near the outlet, for detecting an increase in pressure in the channel means.

16. Apparatus as in claim 15 wherein the gasket membrane is caused to bulge when pressure in the channel means increases, and wherein said over-pressure sensing means comprises means for detecting bulges in the gasket membrane.

17. Apparatus as in claim 13 further including under-pressure sensing means disposed adjacent a part of the gasket membrane forming a side of the channel means, near the inlet, for detecting a decrease in pressure in the channel means.

18. Apparatus as in claim 17 wherein the gasket membrane is caused to deflect inwardly toward the channel means when pressure in the channel means decreases, and wherein said under-pressure sensing means comprises means for detecting deflections of the gasket membrane.

19. Apparatus as in claim 1 further including inlet valve means disposed downstream of the inlet of the channel means to control the flow of fluid into the channel means, and outlet valve means disposed upstream of the outlet of the channel means to control the flow of fluid out of the channel means, said inlet and outlet valve means being normally closed, and being operable to selectively open under control of the programmable control means when the pump means is being operated.

20. Apparatus as in claim 19 wherein said inlet and outlet valve means each comprises
   a resilient membrane forming one side of at least a portion of the channel means and being deformable into that portion of the channel means to block the flow of fluid,
   nipple means moveable to deform the membrane into the channel means to block the flow of fluid, and moveable away from the channel means to release the membrane and allow the flow of fluid,
   spring means disposed to normally urge the nipple means to deform the membrane, and
   means for selectively moving the nipple means away from the channel means to allow the flow of fluid.

21. Apparatus as in claim 20 wherein said resilient membrane is comprised of polymeric material.

22. Apparatus as in claim 20 wherein said resilient membrane is comprised of a material selected from the group consisting of silicone, polyurethane, and natural rubber, polysiloxene-modifier, styrene/ethylene-butylene/styrene, and EPDM/polypropylene alloy.

23. Apparatus as in claim 20 wherein said nipple means comprises
   an elongate lever having a first end and second end and mounted to pivot about an axis spaced from a first end, and
   a nipple extending from the first end generally at a right angle from the lever, to contact and deform the membrane when the lever is pivoted to a first position and to release the membrane when the lever is pivoted to a second position.

24. Apparatus as in claim 23 wherein said motor means includes a gear means having a cam track defined thereon, said cam track moving when the motor means is operated, and wherein said moving means comprises,
   an actuation lever mounted to pivot about an axis spaced from one end,
   a push means extending from the actuation lever to contact and move the second end of the elongate lever to the second position, when the actuation lever is pivoted, and
   a cam follower means disposed on the actuation lever to rest on and ride over the cam track and cause the actuation lever to pivot.

25. Apparatus as in claim 24 wherein said spring means is disposed to normally urge the first end of the elongate lever and nipple to contact and deform the membrane.

26. Apparatus as in claim 24 wherein said gear means includes
   an axle means about which the gear means rotates to rotate the cam track, said axle means including a lower end for resting on a support as the gear means is rotated, and
   a support cup bearing for receiving and holding said lower end of the axle means.

27. Apparatus as in claim 26 wherein said lower end of the axle means is generally spherical, and wherein the support cup bearing is generally concave with inverse conical side walls against which the lower end of the axle means rests.

28. Apparatus as in claim 1 further including a filter chamber formed in the channel means and into which fluid flows before exiting through the outlet, and a hydrophilic membrane disposed between the filter chamber and the outlet for filtering the fluid as it flows from filter chamber to the outlet.

29. Apparatus as in claim 28 further including a hydrophobic membrane disposed between the filter membrane and the outside to allow air in the fluid to diffuse therethrough to the outside.

30. Apparatus as in claim 1 wherein the pump means comprises:
   piston means disposed in the third opening of the pump chamber to reciprocate in and out of the pump chamber to pump fluid therethrough, and
   sphincter seal means positioned over the third opening of the pump chamber and about the piston means to prevent fluid from leaking from the pump chamber out the third opening.

31. Apparatus as in claim 30 wherein the pump means further comprises
   crank means coupled to the motor means to rotate when the motor means is operated, and
   connecting means pivotally coupled between the crank means and the piston means to cause the piston means to reciprocate when the crank means is rotated.

32. Apparatus as in claim 1 wherein said motor means includes a drive means shaft for rotating to cause operation of the pump means, said drive means shaft including a lobe thereon, said apparatus further including a switch means operable by the lobe after one revolution of the drive means shaft to turn off the motor means.

* * * * *

UNITED STATES PATENT AND TRADEMARK OFFICE
CERTIFICATE OF CORRECTION

PATENT : 5,807,075
DATED : Sep. 15, 1998
INVENTOR(S) : Jacobsen et al.

It is certified that error appears in the above-identified patent and that said Letters Patent is hereby corrected as shown below:

On the title page, item [75] Inventors: insert the following,
Kent F. Beck of Layton, Ohio Signed and Sealed this Thirteenth Day of June, 2000

Attest:

Q. TODD DICKINSON

*Attesting Officer*     *Director of Patents and Trademarks*